(12) United States Patent
Yamada et al.

(10) Patent No.: US 9,937,336 B2
(45) Date of Patent: Apr. 10, 2018

(54) METHOD OF MANUFACTURING A CONICAL-PROJECTIONS-SHEET PACKAGING BODY

(71) Applicant: NISSHA PRINTING CO., LTD., Kyoto-shi, Kyoto (JP)

(72) Inventors: Shinya Yamada, Kyoto (JP); Osanobu Akao, Kyoto (JP); Masateru Chiyama, Kyoto (JP)

(73) Assignee: NISSHA PRINTING CO., LTD., Kyoto (JP)

( * ) Notice: Subject to any disclaimer, the term of this patent is extended or adjusted under 35 U.S.C. 154(b) by 0 days.

(21) Appl. No.: 15/128,820

(22) PCT Filed: Mar. 13, 2015

(86) PCT No.: PCT/JP2015/057450
§ 371 (c)(1),
(2) Date: Sep. 23, 2016

(87) PCT Pub. No.: WO2015/146627
PCT Pub. Date: Oct. 1, 2015

(65) Prior Publication Data
US 2017/0106179 A1    Apr. 20, 2017

(30) Foreign Application Priority Data

Mar. 26, 2014    (JP) ................. 2014-063851

(51) Int. Cl.
*B65B 9/04*        (2006.01)
*B65B 25/00*       (2006.01)
(Continued)

(52) U.S. Cl.
CPC ........ *A61M 35/00* (2013.01); *A61M 37/0015* (2013.01); *B65B 9/04* (2013.01);
(Continued)

(58) Field of Classification Search
CPC .... B65D 75/32; B65D 75/322; B65D 75/326; A61K 9/7023; A61K 9/703; A61K 9/7038;
(Continued)

(56) References Cited

U.S. PATENT DOCUMENTS 4,751,133 A * 6/1988 Szycher ................. A61L 15/26
                                                    427/2.3
4,782,647 A * 11/1988 Williams ................ B65B 9/023
                                                    53/141
(Continued)

FOREIGN PATENT DOCUMENTS

JP    2007500711 A    1/2007
JP    2010094414 A    4/2010
(Continued)

OTHER PUBLICATIONS

Search Report in the corresponding European Patent Application No. 15769382.1 dated Feb. 15, 2017.
(Continued)

*Primary Examiner* — Andrew M Tecco
*Assistant Examiner* — Praachi M Pathak
(74) *Attorney, Agent, or Firm* — Global IP Counselors, LLP

(57) ABSTRACT

A method of manufacturing a conical-projections-sheet packaging body includes forming a plurality of conical-recess parts on a conical-projections forming sheet; forming, by supplying a conical-projections material to the conical-projections forming sheet, a conical-projections sheet including a base sheet and a plurality of conical projections formed on a surface of the base sheet and disposed inside the plurality of conical-recess parts; forming a plurality of sets of the conical-projections forming sheets and the conical-projections sheets by punching out the conical-projections
(Continued)

forming sheets and the conical-projections sheets; and using a package member to package a set of the conical-projections sheets and the conical-projections forming sheets tightly adhered to one another. Thus, the plurality of conical projections of the conical-projections sheet are protected.

4 Claims, 19 Drawing Sheets

(51) Int. Cl.
  *B65B 63/00* (2006.01)
  *B65D 75/32* (2006.01)
  *A61K 9/70* (2006.01)
  *A61M 35/00* (2006.01)
  *A61M 37/00* (2006.01)
  *B65D 75/58* (2006.01)

(52) U.S. Cl.
  CPC ....... *B65D 75/326* (2013.01); *B65D 75/5855* (2013.01); *A61M 2037/0053* (2013.01); *A61M 2207/00* (2013.01); *A61M 2209/06* (2013.01)

(58) Field of Classification Search
  CPC ...... A61K 9/7084; A61K 9/7092; B65B 9/04; B65B 25/00; B65B 63/00
  USPC ........... 206/461, 471, 438–440; 53/435, 513, 53/520
  See application file for complete search history.

(56) References Cited

U.S. PATENT DOCUMENTS

| | | | | |
|---|---|---|---|---|
| 5,938,032 A * | 8/1999 | Svec | ........................ | B65B 9/02 206/484 |
| 5,950,830 A * | 9/1999 | Trigger | ................. | A61K 9/703 206/440 |
| 5,965,154 A * | 10/1999 | Haralambopoulos | .. | A61K 9/703 424/447 |
| 6,576,307 B2 * | 6/2003 | Otsu | ................. | A45D 40/0087 206/823 |
| 6,656,147 B1 * | 12/2003 | Gertsek | ............. | A61M 5/14248 604/185 |
| 6,871,477 B1 * | 3/2005 | Tucker | ................. | A61K 9/7023 53/201 |
| 9,566,423 B2 * | 2/2017 | Ueno | .................... | A61K 9/0021 |
| 2005/0025818 A1 | 2/2005 | Gale | | |
| 2008/0262444 A1 * | 10/2008 | Takada | ............... | A61M 37/0015 514/1.1 |
| 2009/0182306 A1 * | 7/2009 | Lee | ....................... | A61K 9/0021 604/506 |
| 2010/0168715 A1 * | 7/2010 | Cassemeyer | ....... | A61M 37/0015 604/520 |
| 2010/0256568 A1 * | 10/2010 | Frederickson | .... | A61M 37/0015 604/173 |
| 2013/0018279 A1 * | 1/2013 | Plante | .............. | A61B 5/150022 600/583 |
| 2014/0243788 A1 * | 8/2014 | Cantor | ............. | A61M 37/0015 604/506 |
| 2015/0051548 A1 * | 2/2015 | Bureau | ............. | A61M 37/0015 604/140 |
| 2017/0106179 A1 * | 4/2017 | Yamada | ................ | A61M 35/00 |

FOREIGN PATENT DOCUMENTS

| | | |
|---|---|---|
| JP | 2013244341 A | 12/2013 |
| WO | 2007075806 A2 | 7/2007 |
| WO | 2011002034 A1 | 1/2011 |

OTHER PUBLICATIONS

International Search Report in PCT/JP2015/057450 dated Jun. 16, 2015.

* cited by examiner

METHOD OF MANUFACTURING A CONICAL-PROJECTIONS-SHEET PACKAGING BODY

CROSS-REFERENCE TO RELATED APPLICATION

This U.S. National stage application claims priority under 35 U.S.C. § 119(a) to Japanese Patent Application No. 2014-063851, filed in Japan on Mar. 26, 2014, the entire contents of Japanese Patent Application No. 2014-063851 are hereby incorporated herein by reference.

BACKGROUND

Field of the Invention

The present invention relates to a method of manufacturing a conical-projections-sheet packaging body including a plurality of conical projections.

Background Art

A resin sheet having a plurality of minute recessed parts are utilized as, for example, a conical-projections forming mold for manufacturing a plurality of conical projections on a conical-projections sheet (e.g., refer to PCT International Publication No. WO2011/002034). Furthermore, one example of a conical-projections sheet is a transdermal patch. A transdermal patch is used as one means of noninvasively administering a drug or the like via the body surface of an organism, such as the skin or a mucous membrane. In such a case, the drug is adhered to the conical projections.

SUMMARY

Each conical projection of the plurality of conical projections of the conical-projections sheet has a minute shape that is relatively easily damaged. Furthermore, after a completed conical-projections sheet is packaged and ready to be shipped and transported, it is necessary to take measures to ensure that the conical projections do not get damaged. However, an effective measure to protect the conical projections inside the packaging has yet to be proposed.

An object of the present invention is to protect a plurality of conical projections of a conical-projections sheet.

Aspects of the present invention are explained below as the technical solution. These aspects can be arbitrarily combined as needed.

A method of manufacturing a conical-projections-sheet packaging body according to one aspect of the present invention includes the following steps:

forming a plurality of conical-recess parts on a conical-projections forming sheet;

forming, by supplying a conical-projections material to the conical-projections forming sheet, a conical-projections sheet including a substrate and a plurality of conical projections formed on a surface of the base sheet and disposed inside the plurality of conical-recess parts;

forming a plurality of sets of the conical-projections forming sheets and the conical-projections sheets by punching out the conical-projections forming sheets and the conical-projections sheets; and using a package member to package a set of the conical-projections sheets and the conical-projections forming sheets tightly adhered to one another.

In this manufacturing method, the conical-projections sheet is formed in the conical-projections forming sheet, and that state when formed is maintained. Specifically, the plurality of conical projections of the conical-projections sheet are formed by the plurality of conical-recess parts of the conical-projections forming sheet and is also subsequently protected by the plurality of conical-recess parts. That is, the plurality of conical projections of the conical-projections sheet is reliably protected.

In addition, this manufacturing method further include: punching out the conical-projections forming sheets and the conical-projections sheets to form a plurality of sets of the conical-projections forming sheets and the conical-projections sheets, and therefore the plurality of conical-projections-sheet packaging bodies can be manufactured in a short time.

The method of manufacturing may further include: fixing a support body to a second surface of the base sheet of the conical-projections sheet. Furthermore, this step may be performed before or after the punching step.

The punching step may include forming a protruding portion, which protrudes from the conical-projections sheet in a horizontal direction, on the support body; and the packaging step may include positioning the support body, the conical-projections sheet, and the conical-projections forming sheet inside the package member by adhering the protruding portion to part of the package member.

In this manufacturing method, the positioning of the conical-projections sheet, etc. inside the package member is performed by adhering the support body to part of the package member, and therefore the plurality of conical projections of the conical-projections sheet can be protected with a simple structure and method.

In addition, if the user peels the protruding portion of the support body from the package member, then the support body, the conical-projections sheet, and the conical-projections forming sheet are removed from the package member.

The packaging step may include: positioning the support body, the conical-projections sheet, and the conical-projections forming sheet inside the package member by fixing the conical-projections forming sheet to the package member.

In this manufacturing method, because the positioning of the conical-projections sheet, etc. inside the package member is accomplished by the fixing of the conical-projections forming sheet to the package member, the plurality of conical projections of the conical-projections sheet can be protected with a simple structure and method.

In addition, if the user holds and moves the support body such that the support body separates from the package member, then the conical-projections sheet separates from the conical-projections forming sheet together with the support body. Thereby, the conical-projections sheet is obtained in the state wherein the plurality of conical projections are exposed.

The punching step may be performed such that the conical-projections forming sheet has a main-body part, whereto the plurality of conical projections are tightly adhered, and a grasp part arranged to protrude from the main-body part in the horizontal direction and is used for peeling the conical-projections forming sheet from the conical-projections sheet.

In this manufacturing method, after the conical-projections forming sheet and the conical-projections sheet have been peeled from the package member, it becomes easy to peel the conical-projections forming sheet from the conical-projections sheet by grasping the grasp part.

In a conical-projections-sheet packaging body and a method of manufacturing the same according to the present invention, a plurality of conical projections of a conical-projections sheet can be reliably protected.

DESCRIPTION OF EMBODIMENTS (1) Conical-Projections-Sheet Packaging Body

Figure 1:
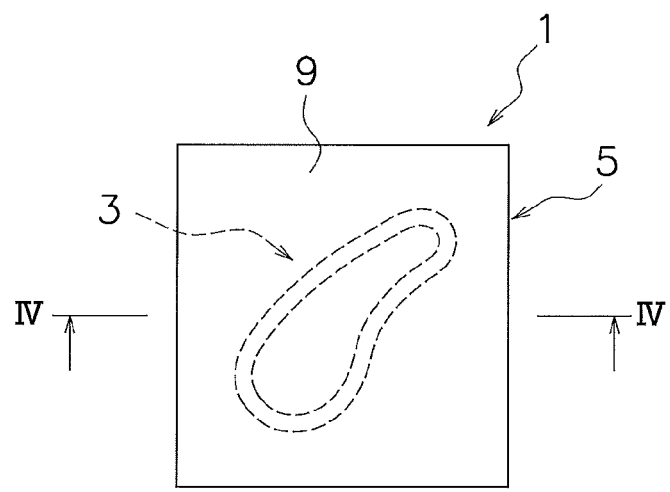
FIG. 1 is a plan view of a conical-projections-sheet packaging body according to one embodiment of the present invention.
Figure 2:
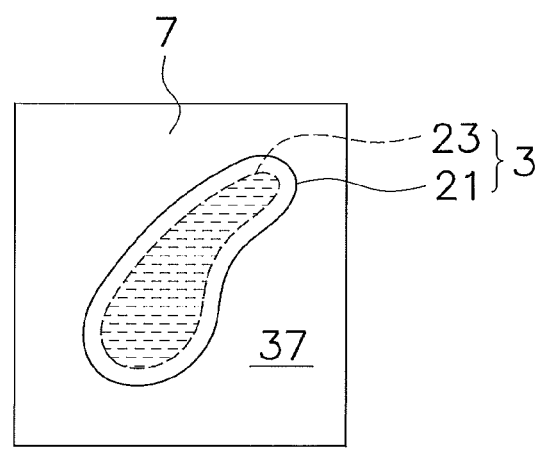
FIG. 2 is a plan view of the state in which a sealing sheet has been peeled from the conical-projections-sheet packaging body.
Figure 3:
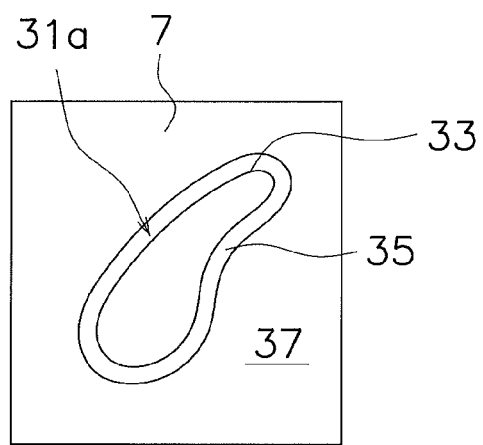
FIG. 3 is a plan view of the state in which a conical-projections sheet has been peeled from the conical-projections-sheet packaging body.
Figure 4:
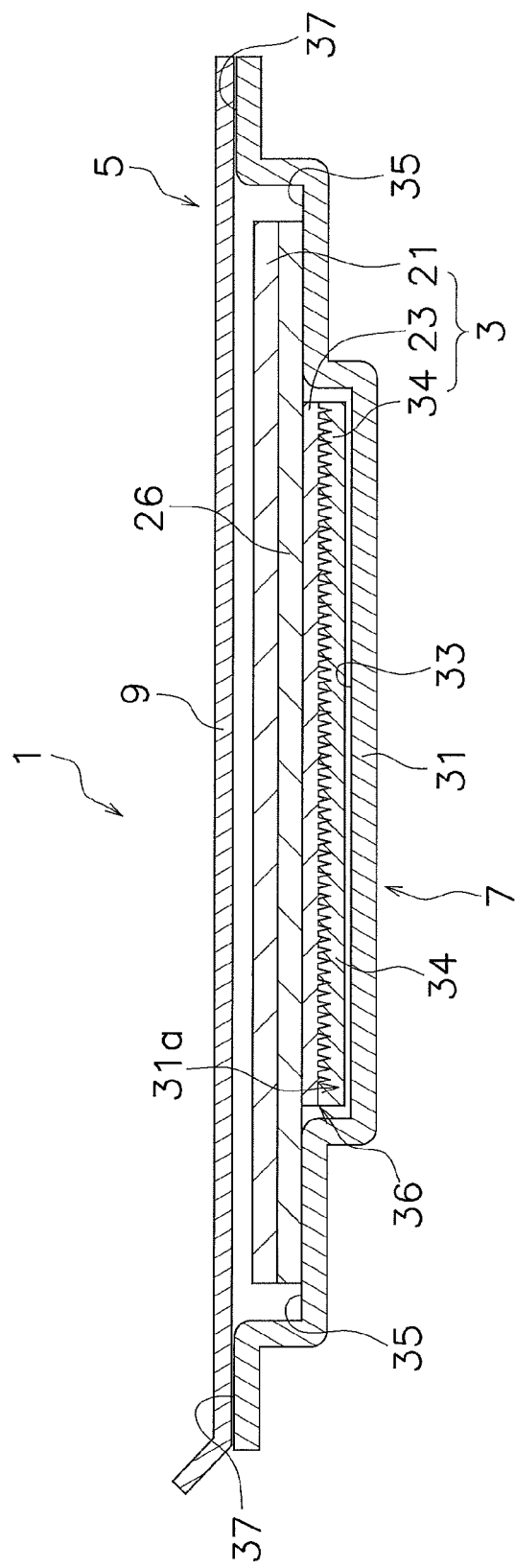
FIG. 4 is a cross-sectional view taken along line IV-IV in FIG. 1 and is a cross-sectional view of the conical-projections-sheet packaging body.
Figure 5:
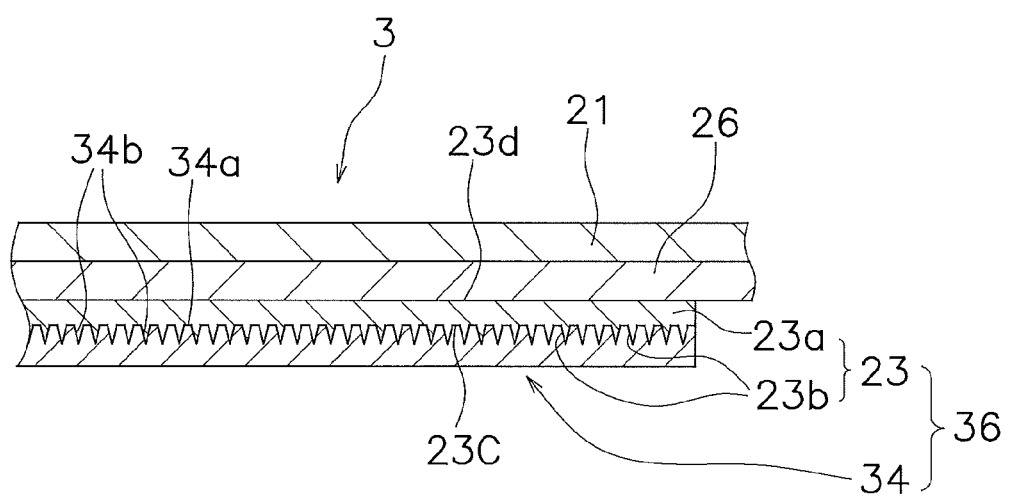
FIG. 5 is a partial, enlarged view of FIG. 4.

A conical-projections-sheet packaging body 1 according to the present embodiment will now be explained, with reference to FIG. 1 to FIG. 5. FIG. 1 is a plan view of the conical-projections-sheet packaging body according to one embodiment of the present invention. FIG. 2 is a plan view of the state in which a sealing sheet has been peeled from the conical-projections-sheet packaging body. FIG. 3 is a plan view of the state in which a conical-projections sheet has been peeled from the conical-projections-sheet packaging body. FIG. 4 is a cross-sectional view taken along line IV-IV in FIG. 1 and is a cross-sectional view of the conical-projections-sheet packaging body. FIG. 5 is a partial, enlarged view of FIG. 4.

The conical-projections-sheet packaging body 1 includes a plurality of support-body-attached, conical-projections sheets 3 and a package member 5, which packages the support-body-attached, conical-projections sheets 3. Furthermore, in the embodiment below, one support-body-attached, conical-projections sheet 3 is housed inside the conical-projections-sheet packaging body 1, but a plurality of the support-body-attached, conical-projections sheets 3 may be housed.

(1-1) Support-Body-Attached, Conical-Projections Sheet

The support-body-attached, conical-projections sheet 3 is a member that is packaged by the package member 5 and is used after being removed from the package member 5 as needed. The support-body-attached, conical-projections sheet 3 is a sheet-shaped article that principally includes a support body 21 and a conical-projections sheet 23. In addition, the support-body-attached, conical-projections sheet 3 further includes a conical-projections forming sheet 34.

The conical-projections sheet 23 is a sheet-shaped article whereon a plurality of conical projections are formed on one surface, which is discussed below. The thickness of the conical-projections sheet 23 is approximately several hundred micrometers. The overall planar shape of the conical-projections sheet 23 is smoothly curved and has a magatama (comma) shape having a portion with a large width and a portion with a small width, as shown in FIG. 2. The shape of the conical-projections sheet 23 may be a circle, an ellipse, a triangle, a quadrangle, a square, or some other shape. If the conical-projections sheet 23 is, for example, a quadrangle, then one side is approximately several to several tens of millimeters.

The structure of the conical-projections sheet 23 will now be further explained, with reference to FIG. 5. The conical-projections sheet 23 includes a sheet-shaped base sheet 23$a$ and a plurality of conical projections 23$b$. The plurality of conical projections 23$b$ are formed on a surface 23$c$ (in the present embodiment, a lower surface) of the base sheet 23$a$. Each conical projection 23$b$ has, for example, a conical shape or a pyramidal shape with a height of 10-1000 μm, wherein the ratio of the cross-sectional diameter, at the base, to the height is 1:0.2-1:5 and the aspect ratio (height/cross-sectional diameter) is high.

The conical-projections sheet 23 is a transdermal patch that is used, for example, to administer a drug or the like by being affixed such that it contacts the skin of a person. Specifically, the administration of the drug or the like is promoted by the base sheet 23a being adhered onto the skin and the conical projections 23b piercing the skin.

The conical-projections sheet 23 consists of, as the principal material, for example, a water-soluble drug, or, a water-soluble macromolecule, such as hyaluronate, a water-soluble collagen, dextran, chondroitin sulfate, or the like, to which a drug is added. Furthermore, the water-soluble macromolecule to which a pharmaceutical agent has been added is preferably an in-vivo-soluble, water-soluble macromolecule, for example, an in-vivo-soluble, water-soluble macromolecule such as sodium chondroitin sulfate, hyaluronate, or dextran.

Furthermore, the water-soluble macromolecule is a substance of at least one selected from the group consisting of sodium chondroitin sulfate, hyaluronate, a collagen (or a hydrolyzed collagen), gelatin, a glycogen, dextran, dextrin, dextran sulfate, cyclodextrin, chitosan, proteoglycan, pullulan, hydroxypropylcellulose, alginic acid, agarose, glycogen, carboxymethyl cellulose, hydroxyethyl cellulose, hydroxypropylcellulose, polyvinylpyrrolidone, polyvinyl alcohol, and a carboxyvinyl polymer. One of these water-soluble macromolecules may be used alone, or a plurality thereof may be used in combination.

The support body 21 is a sheet for supporting the conical-projections sheet 23 and is made of, for example, a resin. The support body 21 is fixed to a second surface 23d of the base sheet 23a of the conical-projections sheet 23 and is further adhered to a packaging member 7 (discussed later).

An adhesive layer 26 is provided on the lower surface of the support body 21. The support body 21 is fixed to the second surface 23d of the conical-projections sheet 23 by the adhesive layer 26.

Furthermore, the adhesive layer 26 is also provided on a portion of the lower surface of the support body 21 that is further radially outward of the conical-projections sheet 23. Accordingly, the support body 21 (that is, the support-body-attached, conical-projections sheet 3) is fixed to the packaging member 7 (discussed later) by the adhesive layer 26.

The conical-projections forming sheet 34 is a member for both forming the conical projections 23b and protecting the conical projections 23b after forming. The conical-projections forming sheet 34 is adhered to the surface 23c of the conical-projections sheet 23. In addition, as shown in FIG. 5, a plurality of conical-recess parts 34b, which are for forming and housing the conical projections 23b of the conical-projections sheet 23, is formed on an upper surface 34a of the conical-projections forming sheet 34. Furthermore, each conical-recess parts 34b is an indentation that is upwardly open but does not pass through the conical-projections forming sheet 34.

Taking into consideration that the conical-projections forming sheet 34 is used as the member that forms the plurality of conical-recess parts 34b, the conical-projections forming sheet 34 consists of, for example, a polyolefin based resin such as polyethylene, polypropylene, and the like.

A conical-projections-sheet, forming-and-protecting-structure 36 (hereinbelow, called the forming-and-protecting-structure 36) is constituted by the conical-projections sheet 23 and the conical-projections forming sheet 34, which are tightly adhered to one another as discussed above.

(1-2) Package Member

The package member 5 is a member for packaging the support-body-attached, conical-projections sheets 3. The package member 5 includes the packaging member 7 and a sealing sheet 9; the support-body-attached, conical-projections sheet 3 is packaged by the two sheets being adhered together.

The packaging member 7 is a sheet-shaped member and is composed of a common resin material. As shown in FIG. 4, the packaging member 7 includes a housing part 31 for housing the support-body-attached, conical-projections sheet 3. The housing part 31 has a protruding shape that bulges toward the outer side of the package member 5, and a recessed-housing part 31a is formed on the inner side of the package member 5. The planar shape of the recessed-housing part 31a is the same as the planar shape of the support-body-attached, conical-projections sheet 3, as shown in FIG. 3. The recessed-housing part 31a has a bottom surface 33 and therearound a ring-shaped stepped surface 35 that is higher than the bottom surface 33. A flat surface 37 is provided around the recessed-housing part 31a (that is, around the stepped surface 35). Thus, the recessed-housing part 31a, which has a recessed shape, of the housing part 31 has a stepped shape that is formed by the bottom surface 33, the ring-shaped stepped surface 35, and the flat surface 37. The ring-shaped, outer-perimeter part (protruding portion) of the support body 21 is adhered to the ring-shaped, stepped surface 35 via the adhesive layer 26. Furthermore, the stepped surface 35 may be coated with a die-releasing agent to make it easy for the outer-perimeter part of the support body 21 to be peeled off.

Thus, because the outer-perimeter part (the protruding portion), which protrudes from the conical-projections sheet 23 in the horizontal direction, is formed on the support body 21, the support body 21, the conical-projections sheet 23, and the conical-projections forming sheet 34 is positioned inside the package member 5 by adhering that outer-perimeter part to the packaging member 7. Thus, the positioning of the conical-projections sheet 23, etc. inside the package member 5 is performed by adhering the support body 21 to part of the package member 5, and therefore the plurality of conical projections 23b of the conical-projections sheet 23 can be protected with a simple structure and method.

The support-body-attached, conical-projections sheet 3 discussed above is housed in the recessed-housing part 31a of the housing part 31. Specifically, the forming-and-protecting-structure 36 (the conical-projections sheet 23 and the conical-projections forming sheet 34) is disposed in a space that corresponds to the bottom surface 33; as a result, the conical-projections forming sheet 34 is disposed at a position proximate to and spaced apart from the bottom surface 33.

The sealing sheet 9 is a sheet-shaped member that is adhered to the inner-side surface of the packaging member 7 in order to seal the support-body-attached, conical-projections sheet 3 inside the recessed-housing part 31a between the sealing sheet 9 and the packaging member 7. Specifically, the sealing sheet 9 includes, for example, as a general structure, a surface-resin layer (not shown) and a metal layer (not shown). The surface-resin layer is capable of being printed upon and further functions to protect the metal layer. The metal layer is provided on a lower surface of the surface-resin layer. The metal layer consists of aluminum or an alloy thereof and has a high degree of moisture proofness.

A bonding layer (not shown) is provided on a surface on the side of the metal layer opposite the surface-resin layer.

The bonding layer is for bonding the sealing sheet 9 to the packaging member 7; specifically, the sealing sheet 9 is bonded to the flat surface 37 of the packaging member 7.

Thus, the sealing sheet 9 is adhered to the inner-side surface of the packaging member 7 in the state wherein the sealing sheet 9 covers the conical-projections sheet 23, and thereby the sealing sheet 9 and the packaging member 7 seal the recessed-housing part 31a.

In the conical-projections-sheet packaging body 1 discussed above, the conical projections 23b of each conical-projections sheet 23 are formed by the plurality of conical-recess parts 34b of the conical-projections forming sheet 34 (discussed below) and subsequently are also protected by the conical-projections forming sheet 34.

Figure 6:
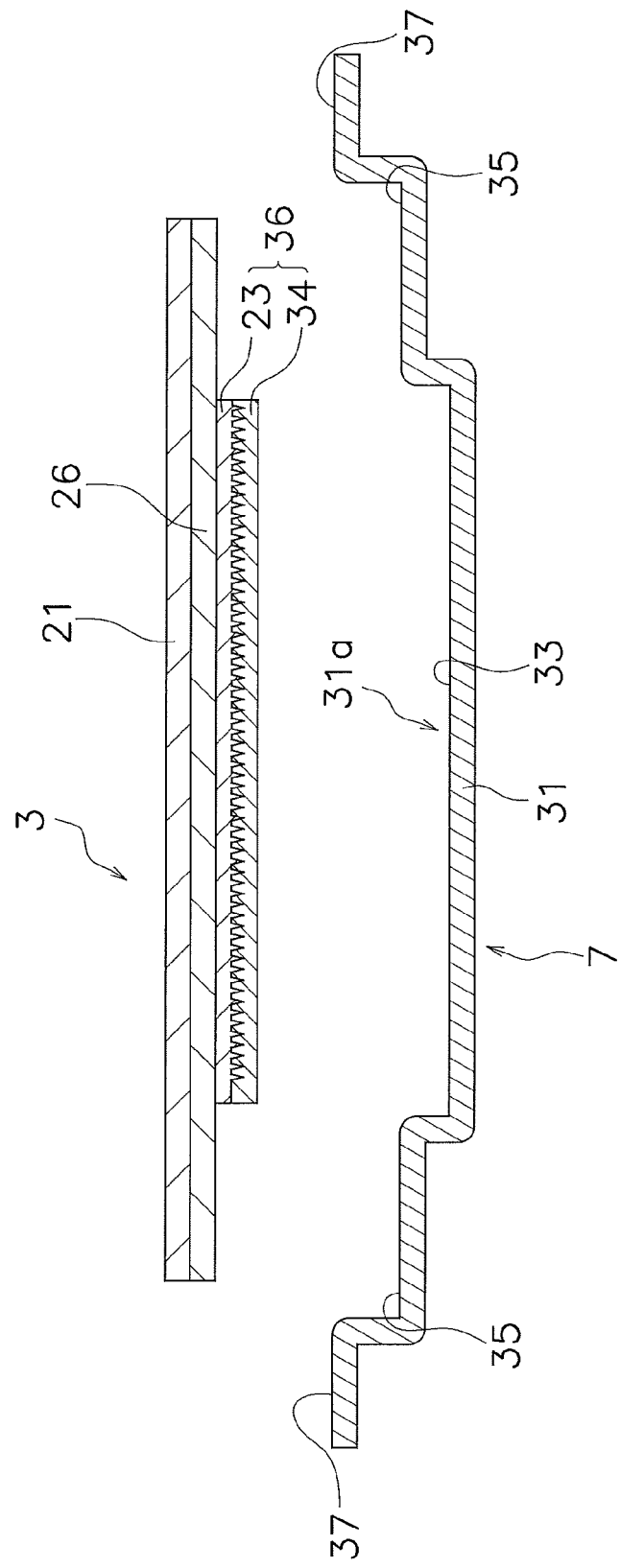
FIG. 6 is a cross-sectional view that shows the state wherein a support-body-attached, conical-projections sheet has been peeled from the package member.

As shown in FIG. 6, when removing the support-body-attached, conical-projections sheet 3 from the conical-projections-sheet packaging body 1, a user peels the sealing sheet 9 from the packaging member 7 and subsequently peels the support-body-attached, conical-projections sheet 3 from the packaging member 7. In other words, if the user peels the outer-perimeter part of the support body 21 from the package member 5, then the support body 21, the conical-projections sheet 23, and the conical-projections forming sheet 34 are removed from the package member 5. Thereby, the conical-projections sheet 23, in which the plurality of conical projections 23b are protected by the conical-projections forming sheet 34, can be obtained. FIG. 6 is a cross-sectional view that shows the state in which a packaging member has been peeled from the support-body-attached, conical-projections sheet.

Figure 7:
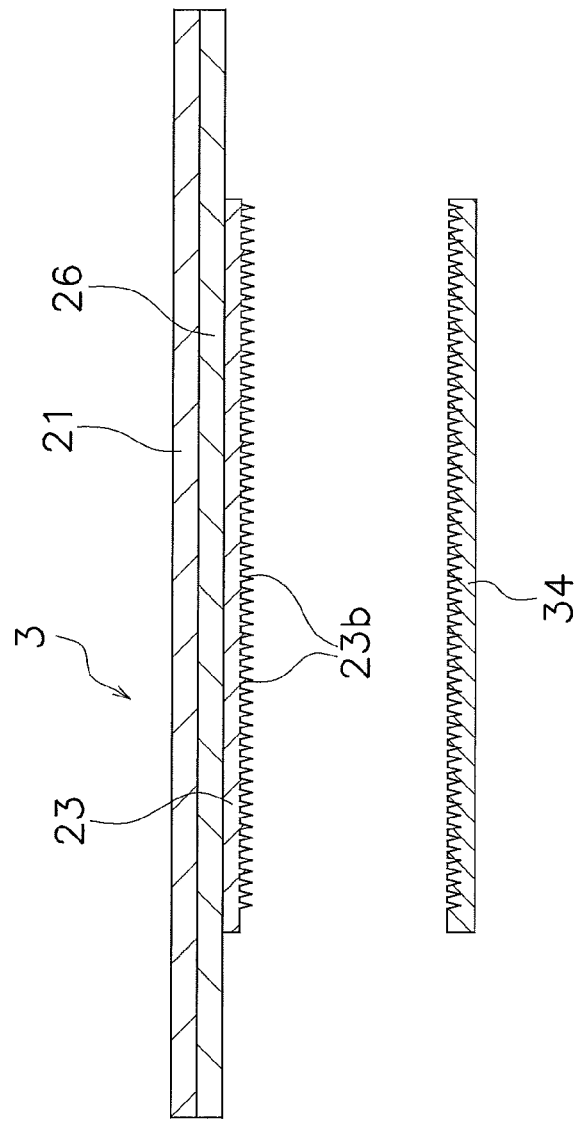
FIG. 7 is a cross-sectional view that shows the state wherein a conical-projections forming sheet has been peeled from the support-body-attached, conical-projections sheet.

Next, as shown in FIG. 7, the user peels the conical-projections forming sheet 34 from the conical-projections sheet 23. FIG. 7 is a cross-sectional view that shows the state wherein the conical-projections forming sheet has been peeled from the support-body-attached, conical-projections sheet. As a result, the user becomes able to use the support-body-attached, conical-projections sheet 3 in accordance with its purpose. In the case of a transdermal patch, the support-body-attached, conical-projections sheet 3 is adhered to the skin of a person. In this case, the outer-perimeter part of the support body 21 adheres to the skin via the adhesive layer 26, and the conical projections 23b of the first adhesive layer 26 contact the skin. That is, the first adhesive layer 26 functions as an adhesive portion after the support-body-attached, conical-projections sheet 3 has been taken out.

(2) Method of Manufacturing the Conical-Projections-Sheet Packaging Body

A method of manufacturing the conical-projections-sheet, forming-and-protecting structure will now be explained, with reference to FIG. 8 to FIG. 22. The plurality of manufacturing processes are explained below.

Figure 8:
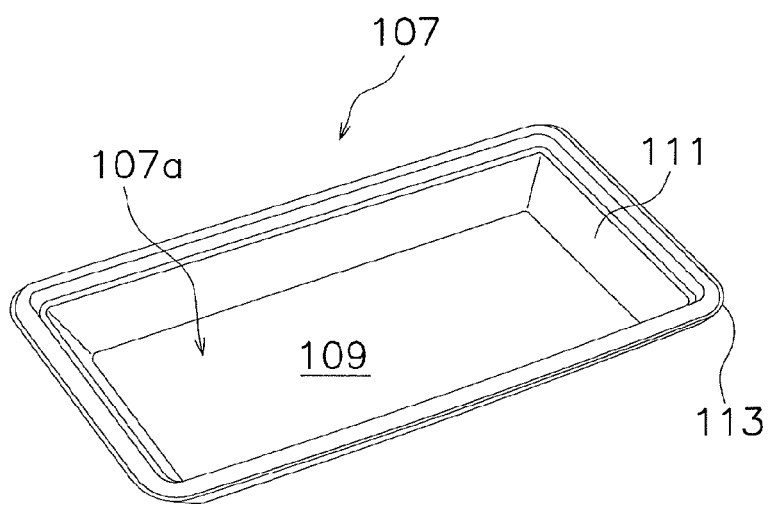
FIG. 8 is an oblique view of a blank of the conical-projections forming sheet.
Figure 9:
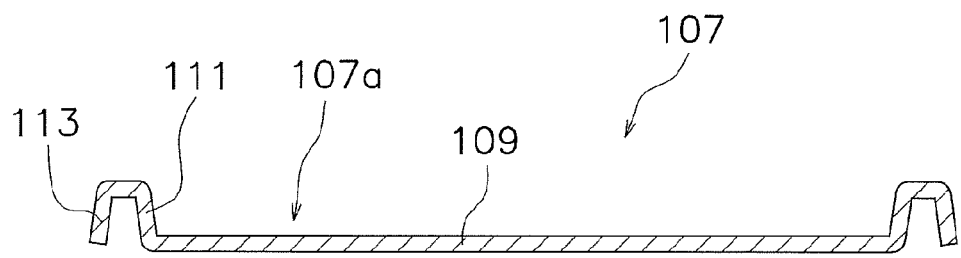
FIG. 9 is a cross-sectional view of the blank of the conical-projections forming sheet.

(2-1) Manufacture of Conical-Projections-Sheet, Forming-and-Protecting-Structure Preform First, as shown in FIG. 8 and FIG. 9, a blank 107, which will constitute the conical-projections forming sheet 34, is prepared. FIG. 8 is an oblique view of a blank of the conical-projections forming sheet. FIG. 9 is a cross-sectional view of a blank of the conical-projections forming sheet. As is clear from the figures, the blank 107 includes a bottom-surface part 109 and side-surface parts 111. The bottom-surface part 109 is, for example, a quadrangular, flat, plate-shaped portion. The side-surface parts 111 are plate-shaped portions that extend upward from four sides of the bottom-surface part 109 and form a recessed part 107a. Furthermore, a folded part 113 is formed over the entire perimeter at upper ends of the side-surface parts 111. In a cross section, the folded part 113 extends toward the outer-perimeter side from the recessed part 107a and further extends downward.

Figure 10:
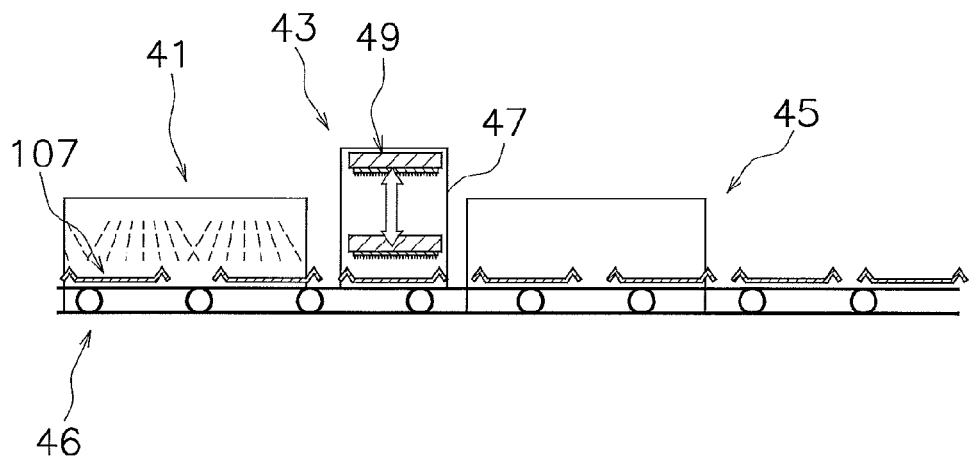
FIG. 10 is a schematic drawing that illustrates a preheating and forming process.
Figure 11:
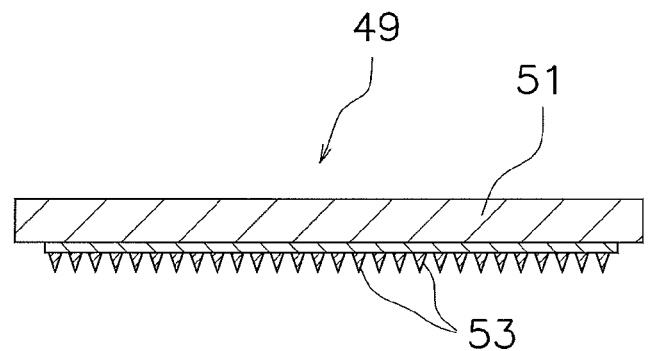
FIG. 11 is a cross-sectional view of a press die.

A process of preheating and forming the blank 107 will now be explained, with reference to FIG. 10 to FIG. 12. FIG. 10 is a schematic drawing that illustrates the preheating and forming process. As shown in the figure, a heating chamber 41, a forming apparatus 43, and a cooling chamber 45 are provided in series.

In the heating chamber 41, the blank 107 is preheated prior to being formed. The forming apparatus 43 forms the conical-recess parts 34b on the blank 107. In the cooling chamber 45, the blank 107 is cooled. The blank 107 is transported between the apparatuses by a conveyor 46.

The forming apparatus 43 is an apparatus for forming the plurality of minute conical-recess parts 34b on the bottom-surface part 109 of the blank 107. As shown in the figure, the forming apparatus 43 includes a high-precision press 47 and a pincushion-shaped press die 49 (a micro-spike die). As shown in FIG. 11, the press die 49 includes a press part 51. FIG. 11 is a cross-sectional view of the press die. The press part 51 has a shape that matches the bottom-surface part 109 of the blank 107, and, on its lower surface, the press part 51 includes a plurality of fabricating projections 53.

Figure 12:
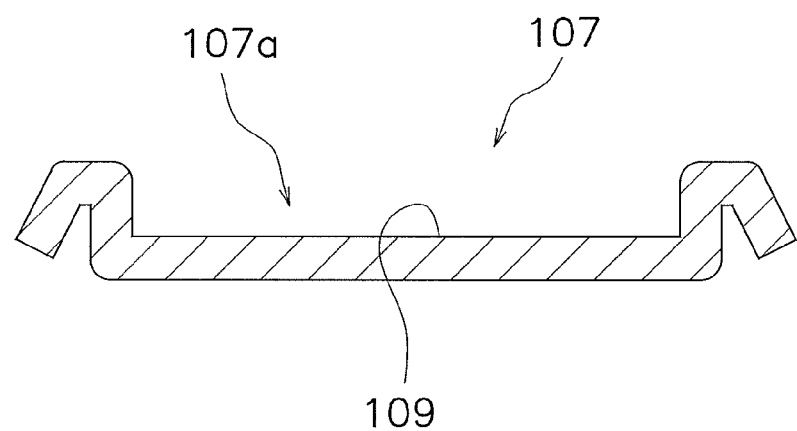
FIG. 12 is a schematic cross-sectional view that shows the state before the forming of the blank.

As shown in FIG. 12, prior to the forming work, the bottom-surface part 109 of the blank 107 is flat. FIG. 12 is a schematic cross-sectional view that shows the state prior to the forming of the blank.

Figure 13:
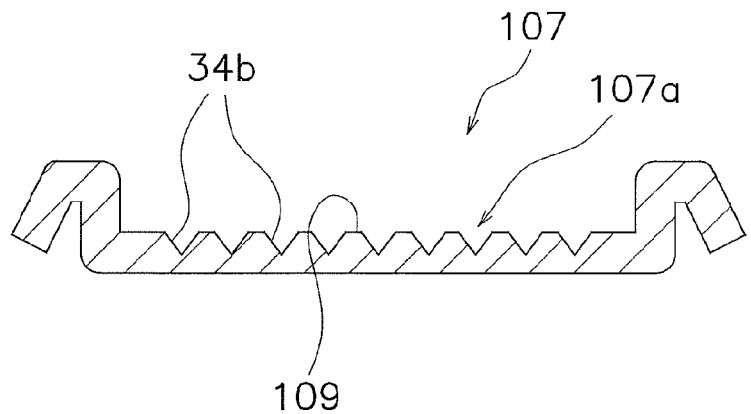
FIG. 13 is a schematic cross-sectional view that shows the state after the forming of the blank.

Owing to the preheating prior to the forming, the blank 107 has already been softened when the press die 49 contacts the bottom-surface part 109. As a result, as shown in FIG. 13, the fabricating projections 53 form the plurality of conical-recess parts 34b on the bottom-surface part 109. Furthermore, the control of the press is formed by a machine capable of controlling the pressing location, the pressing pressure, the pressing time, and the like with high precision.

FIG. 13 is a schematic cross-sectional view that shows the state after the forming of the blank. As shown in the figure, each conical-recess part 34b has, for example, a conical shape or a pyramidal shape and is open toward the upper side in the figure.

Figure 14:
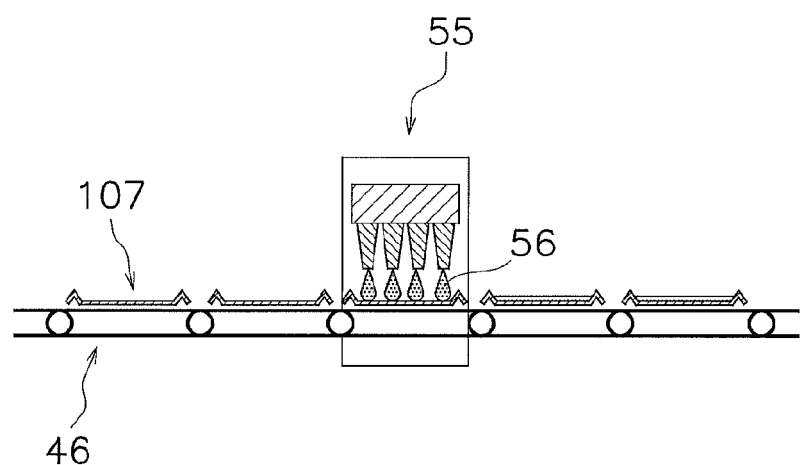
FIG. 14 is a schematic drawing for explaining a process of dripping a conical-projections material onto the conical-projections forming sheets.
Figure 15:
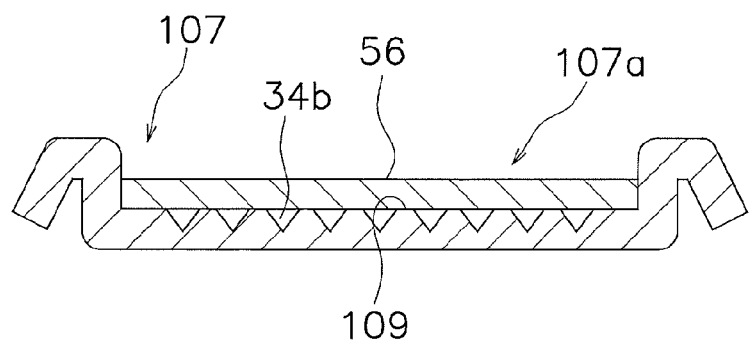
FIG. 15 is a schematic cross-sectional view of the conical-projections forming sheet filled with the conical-projections material.

Next, the process in which a conical-projections material 56 is supplied to the blanks 107 will be explained, with reference to FIG. 14 to FIG. 15. FIG. 14 is a schematic drawing for explaining a process of dripping a conical-projections material onto the conical-projections forming sheets. As shown in the figure, a dispenser 55 is provided. The dispenser 55 is an apparatus that drips the conical-projections material 56 onto the recessed part 107a, thereby filling the recessed part 107a with the conical-projections material 56. The conical-projections material 56 is, for example, sodium hyaluronate dissolved in a solvent consisting of water, etc. Furthermore, a medium wherein water-soluble macromolecules in addition to water are soluble is selected as the solvent. Thus, by supplying the conical-projections material to each bottom-surface part 109, each bottom-surface part 109 is covered by the conical-projections material 56, as shown in FIG. 15. FIG. 15 is a schematic cross-sectional view of the conical-projections forming sheet filled with the conical-projections material. Furthermore, in the present embodiment, the conical-projections material 56 does not penetrate to the interior of the conical-recess parts 34b, and consequently air remains in the conical-recess parts 34b.

Figure 16:
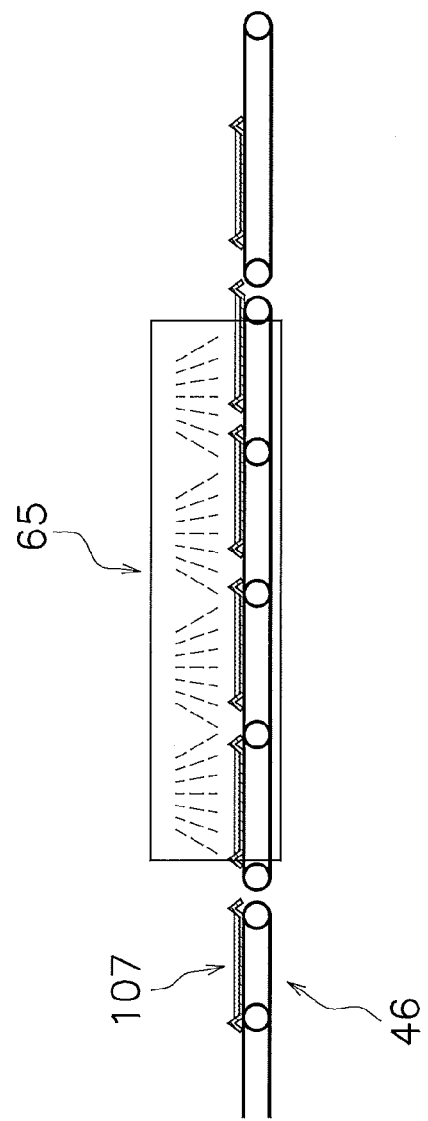
FIG. 16 is a schematic thawing for explaining a process of drying the conical-projections material.
Figure 17:
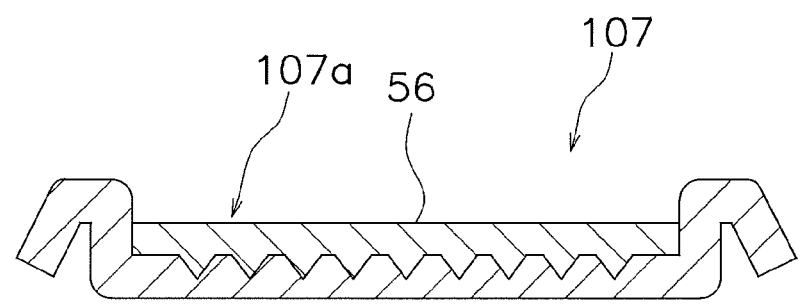
FIG. 17 is a schematic cross-sectional view of the conical-projections forming sheet filled with the conical-projections material before the drying process.
Figure 18:
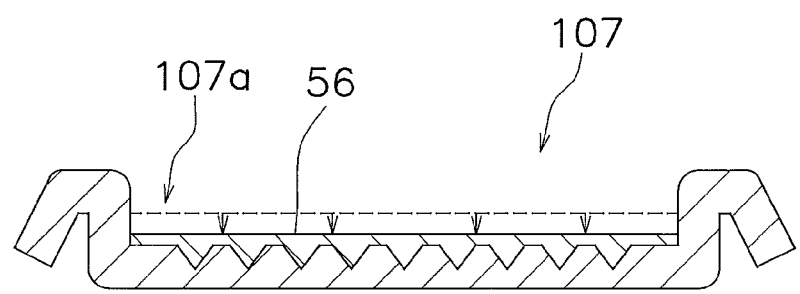
FIG. 18 is a schematic cross-sectional view of the conical-projections forming sheet filled with the conical-projections material after the drying process.

Next, a process of drying and hardening the conical-projections material 56 will be explained, with reference to FIG. 16 to FIG. 18. FIG. 16 is a schematic drawing for explaining a process of drying the conical-projections material. As shown in the figure, a drying furnace 65 is provided. In the drying furnace 65, the conical-projections material 56 for each of the blanks 107 is heated and thereby dried. Thereby, moisture and the solvent agent are evaporated from the conical-projections materials 56. As a result, starting from the state shown in FIG. 17, the conical-projections material 56 shrinks because of the drying, and the volume is reduced to the position shown in FIG. 18. In this state, the conical-projections material 56 becomes the conical projection sheet 23 having the plurality of conical projections 23b. FIG. 17 is a schematic cross-sectional view of the conical-projections forming sheet filled with the conical-projections material prior to the drying process. FIG. 18 is a schematic cross-sectional view of the conical-projections forming sheet filled with the conical-projections material after the drying process.

Figure 19:
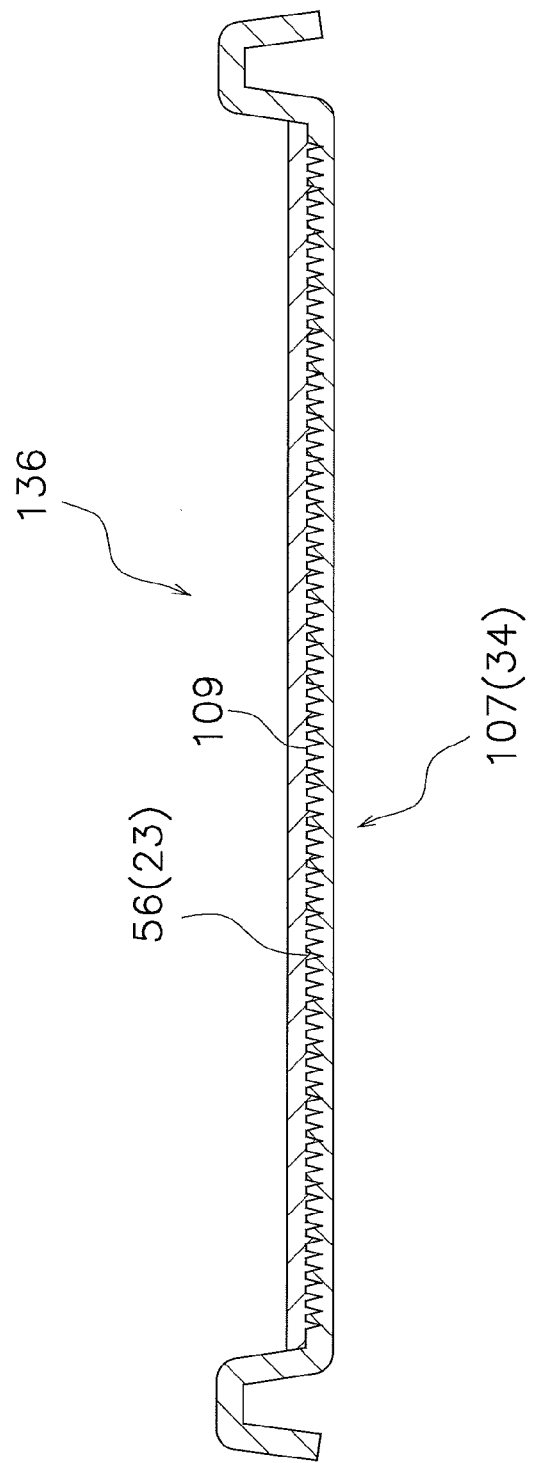
FIG. 19 is a cross-sectional view of a conical-projections-sheet, forming-and-protecting-structure preform.

As a result of the above, as shown in FIG. 19, a conical-projections-sheet, forming-and-protecting-structure preform 136 (hereinbelow, called a preform 136) is obtained wherein is formed the conical-projections material 56 (the conical-projections sheet 23) solidified on the bottom-surface part 109 of the blank 107. FIG. 19 is a cross-sectional view of the conical-projections-sheet, forming-and-protecting-structure preform.

(2-2) Manufacture of the Support-Body-Attached, Conical-Projections Sheet

Figure 20:
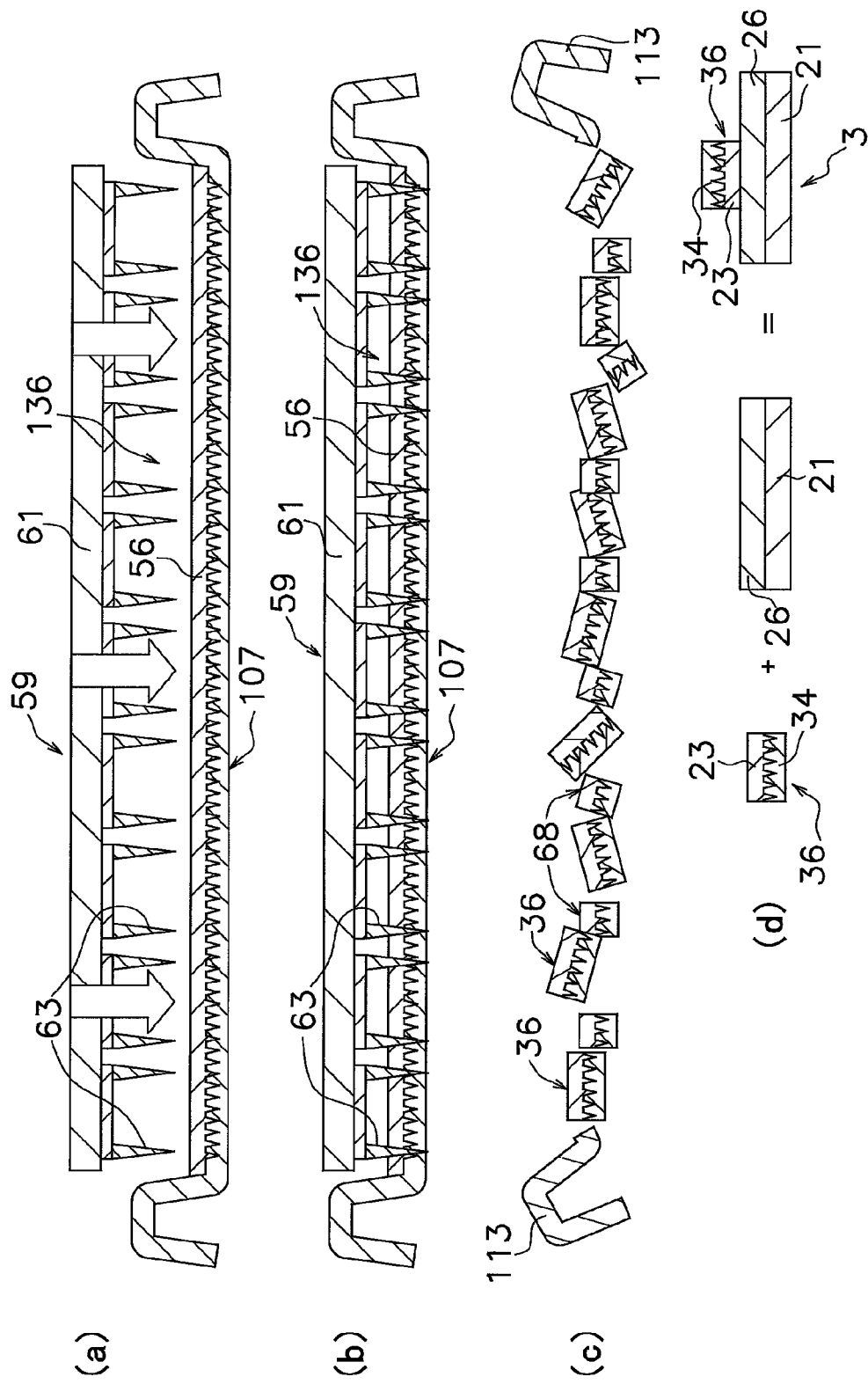
FIG. 20($a$) through 209($d$) include schematic cross-sectional views for explaining a process of manufacturing the support-body-attached, conical-projections sheet from the conical-projections-sheet, forming-and-protecting-structure preform.

FIG. 20 includes schematic cross-sectional views for explaining a process of manufacturing the support-body-attached, conical-projections sheet from the conical-projections-sheet, forming-and-protecting-structure preform. As shown in FIG. 20(*a*), a cutting apparatus 59 is used. The cutting apparatus 59 includes a press part 61 and a plurality of cutting blades 63. The cutting blades 63 are provided on a lower surface of the press part 61. Each cutting blade 63 has a ring shape. As shown in FIG. 20(*b*), when the press part 61 is lowered and brought proximate to the preform 136, the cutting blades 63 cut the preform 136 to the bottom. As a result, as shown in FIG. 20(*c*), the forming-and-protecting-structures 36, which have been punched out in shapes corresponding to the cutting blades 63, are obtained. In addition, waste parts 68 are also obtained at this time. Furthermore, a trimming die, such as a Pinnacle blade, an engraving blade, or a Thomson blade, can be used as the cutting blade. This applies likewise to the cutting blades below.

Lastly, as shown in FIG. 20(*d*), the support body 21 is fixed to the forming-and-protecting-structure 36. Thereby, a plurality of the support-body-attached, conical-projections sheets 3 are obtained.

Because the forming-and-protecting-structures 36, each being a set of a conical-projections forming sheet and a conical-projections sheet, are formed by punching the blank 107, which is the conical-projections forming sheet, and the solidified conical-projections material 56, which is the conical-projections sheet, as described above, the plurality of forming-and-protecting-structures 36 can be manufactured in a short time and with high productivity.

Next, as shown in FIG. 4, the support-body-attached, conical-projections sheet 3 is attached to the recessed-housing part 31*a* of the packaging member 7. Specifically, the outer-perimeter part of the support body 21 is adhered onto the stepped surface 35 via the adhesive layer 26, and thereby the forming-and-protecting-structure 36 is disposed inside the recessed-housing part 31*a*. Lastly, the sealing sheet 9 is bonded to the packaging member 7. As a result, the conical-projections-sheet packaging body 1 is obtained.

Thus, in the state in which the conical-projections-sheet packaging body 1 has been completed, the conical-projections sheet 23 maintains the state in which the conical-projections sheet 23 is fixed to the packaging member 7 by the support body 21 and the adhesive layer 26, and thereby the conical-projections forming sheet 34 is disposed spaced apart from the bottom surface 33. In so doing, the conical projections 23*b* are protected when the conical-projections-sheet packaging body 1 is transported or used.

As discussed above, the conical-projections forming sheet 34 functions as a forming die for forming the conical projections 23*b* of the conical-projections sheet 23. In addition, the conical-projections forming sheet 34 functions as a protective material that protects the conical projections 23*b* of each conical-projections sheet 23.

(3) Second Embodiment

In the first embodiment, the preform 136 is fixed to the support bodies 21 after the preform 136 has been cut up, but the order of the cutting up of the preform 136 and the fixing to the support bodies 21 may be reversed. That is, the step of fixing the support bodies to the second surfaces of the base sheets of the conical-projections sheets may be performed before or after the punching step.

Figure 21:
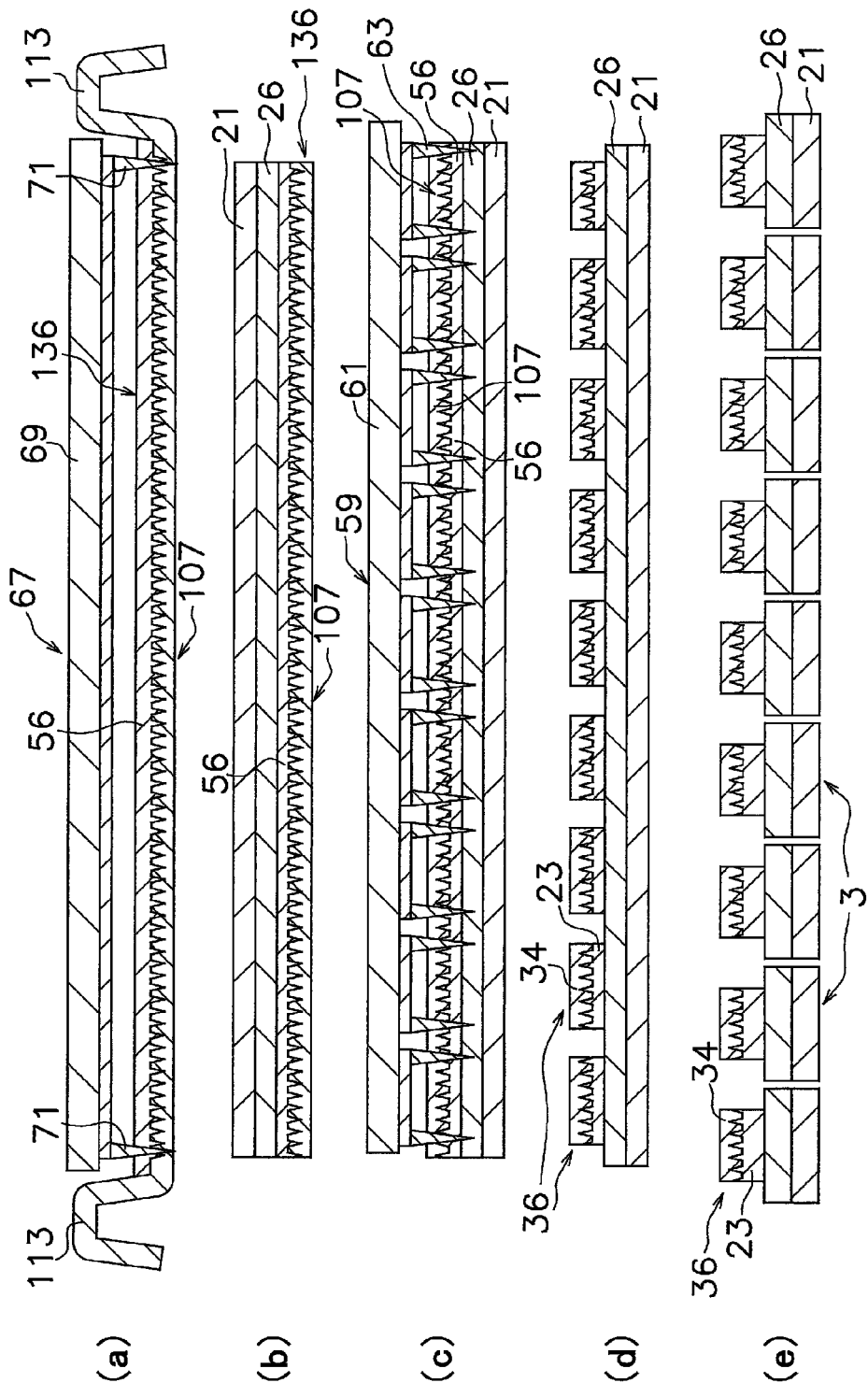
FIG. 21($a$) through 21($e$) include schematic cross-sectional views for explaining a process of manufacturing the support-body-attached, conical-projections sheet from the conical-projections-sheet, forming-and-protecting-structure preform (second embodiment)

The second embodiment is explained below, with reference to FIG. 21. FIG. 21 includes schematic cross-sectional views for explaining a process of manufacturing the support-body-attached, conical-projections sheet from the forming-and-protecting-structure preform of the conical-projections-sheet. Furthermore, details not particularly explained are the same as those in the abovementioned embodiment.

First, as shown in FIG. 19 according to the first embodiment, the preform 136, wherein the conical-projections material 56 (the conical-projections sheet 23) solidified on the bottom-surface part 109 of the blank 107 has been formed, is prepared.

As shown in FIG. 21(*a*), a cutting apparatus 67 is used. The cutting apparatus 67 has a press part 69 and a ring-shaped cutting blade 71. The cutting blade 71 is provided on a lower surface of the press part 69. The cutting blade 71 has a shape that corresponds to the outer perimeter of the bottom-surface part 109 of the blank 107. As shown in FIG. 21(*a*), when the press part 69 is lowered and brought proximate to the preform 136, the cutting blade 71 cuts the preform 136 to the bottom. As a result, the folded part 113 of the blank 107 is cut away. As a result, the preform 136 becomes a planar sheet.

Next, as shown in FIG. 21(*b*), the support body 21, which has a quadrangular shape corresponding to the preform 136, is fixed to the preform 136. That is, the support body 21 is adhered across the entire surface of the preform 136.

Next, as shown in FIG. 21(*c*), the cutting apparatus 59 is used. The cutting apparatus 59 includes the press part 61 and the plurality of cutting blades 63. The cutting blades 63 are provided on a lower surface of the press part 61. Each cutting blade 63 has a ring shape. As shown in FIG. 21(*c*), in the state in which the preform 136 has been inverted, when the press part 61 is lowered and brought proximate to the preform 136, then the cutting blades 63 cut the preform 136 to the bottom. However, the cutting blades 63 do not reach the support body 21; that is, the support body 21 is not cut. As a result, as shown in FIG. 21(*d*), the plurality of forming-and-protecting-structures 36 punched out in shapes corresponding to the plurality of cutting blades 63 are obtained on the support body 21. Furthermore, FIG. 21(*d*) shows the state after the waste parts have been removed.

Furthermore, a cutting apparatus, which is not shown, is used to punch out the support bodies 21 such that the support bodies 21 correspond to the forming-and-protecting-structures 36. As a result, as shown in FIG. 21(e), a plurality of the support-body-attached, conical-projections sheets 3 are obtained.

The second embodiment discussed above obtains the same excellent effects as those in the first embodiment.

(4) Third Embodiment

In the first embodiment and the second embodiment, the conical-projections material 56 (the conical-projections sheet 23), which has been solidified in the preform 136, and the blank 107 are both cut in one cut, but the cutting of the solidified conical-projections material 56 may be performed beforehand.

Figure 22:
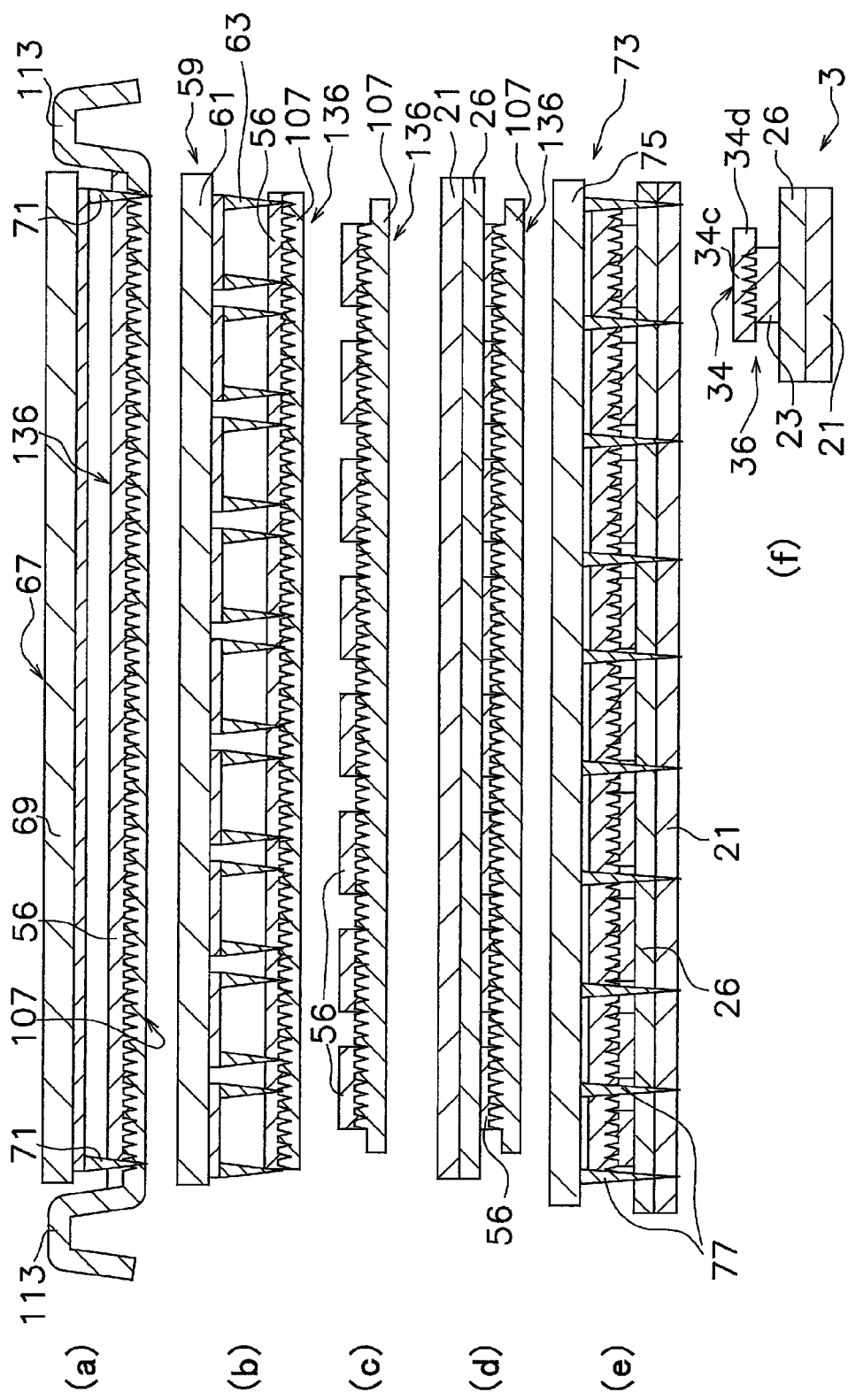
FIG. 22($a$) through 22($e$) include schematic cross-sectional views for explaining a process of manufacturing the support-body-attached, conical-projections sheet from the conical-projections-sheet, forming-and-protecting-structure preform (third embodiment)
Figure 23:
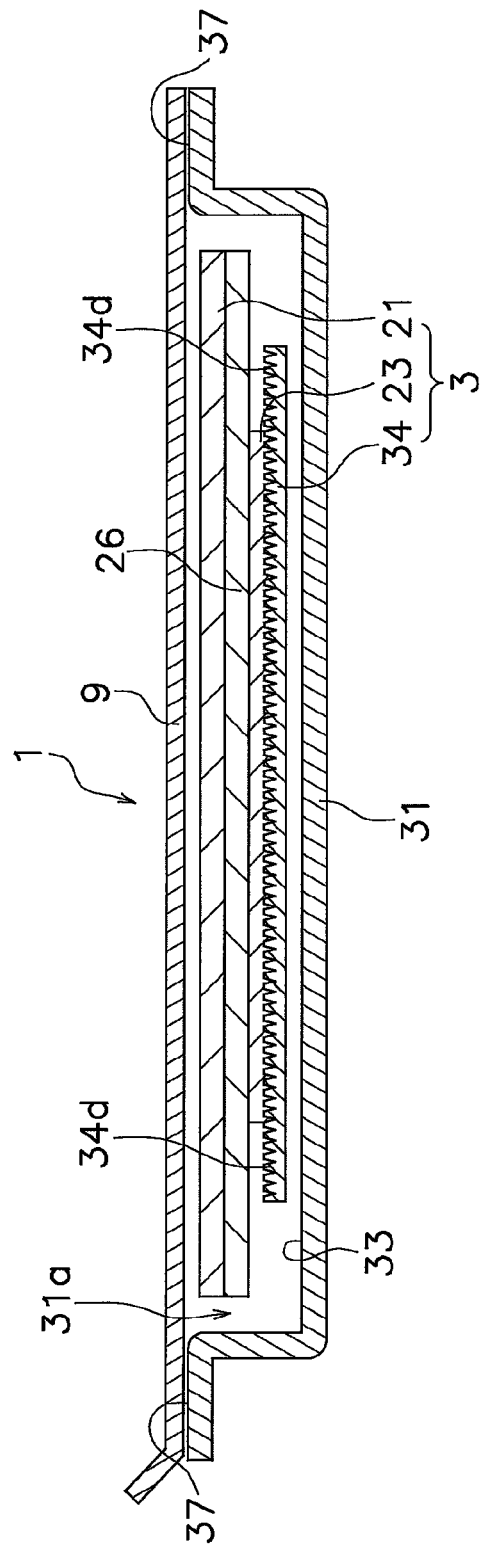
FIG. 23 is a schematic cross-sectional view of the conical-projections-sheet packaging body (third embodiment)

A third embodiment is explained below, with reference to FIG. 22 and FIG. 23. FIG. 22 is schematic cross-sectional views for explaining a process of manufacturing the support-body-attached, conical-projections sheet from the forming-and-protecting-structure preform of the conical-projections-sheet. FIG. 23 is a schematic cross-sectional view of the conical-projections-sheet packaging body. Furthermore, details not particularly explained are the same as those in the abovementioned embodiments.

First, as shown in FIG. 19 according to the first embodiment, the preform 136, wherein the conical-projections material 56 (the conical-projections sheet 23) solidified on the bottom-surface part 109 of the blank 107 has been formed, is prepared.

Next, as shown in FIG. 22(a), the cutting apparatus 67 is used. The cutting apparatus 67 has the press part 69 and the ring-shaped cutting blade 71. The cutting blade 71 is provided on a lower surface of the press part 69. The cutting blade 71 has a shape that corresponds to the outer perimeter of the bottom-surface part 109 of the blank 107. As shown in FIG. 22(a), when the press part 69 is lowered and brought proximate to the preform 136, the cutting blade 71 cuts the preform 136 to the bottom. As a result, the folded part 113 of the blank 107 is cut away. As a result, the preform 136 becomes a planar sheet.

Next, as shown in FIG. 22(b), the cutting apparatus 59 is used. The cutting apparatus 59 includes the press part 61 and the plurality of cutting blades 63. The cutting blades 63 are provided on a lower surface of the press part 61. Each cutting blade 63 has a ring shape. As shown in FIG. 22(b), when the press part 61 is lowered and brought proximate to the preform 136, the cutting blades 63 cut the solidified conical-projections material 56 of the preform 136 to the bottom. However, the cutting blades 63 do not reach the blank 107; that is, the blank 107 is not cut. As a result, as shown in FIG. 22(c), the conical-projections materials 56, which have been punched into shapes corresponding to the cutting blades 63, are obtained on the blank 107. FIG. 22(c) shows the state after the waste parts have been removed.

Next, as shown in FIG. 22(d), the support body 21, which has a quadrangular shape corresponding to the preform 136, is fixed to the conical-projections sheets 23. That is, the support body 21 is adhered across the entire surface of the preform 136.

Next, as shown in FIG. 22(e), a cutting apparatus 73 is used. The cutting apparatus 73 includes a press part 75 and a plurality of cutting blades 77. The cutting blades 77 are provided on a lower surface of the press part 75. Each cutting blade 77 has a ring shape. As shown in FIG. 22(e), in the state in which the preform 136 and the support body 21 have been inverted, when the press part 75 is lowered and brought proximate to the preform 136, the cutting blades 77 cut the preform 136 and the support body 21 to the bottom.

As a result, as shown in FIG. 22(f), a plurality of the support-body-attached, conical-projections sheets 3 are obtained.

In the present embodiment, a grasp part 34d is formed on a main-body part 34c of each conical-projections forming sheet 34. The main-body part 34c is a portion to which the conical projections 23b are tightly adhered. The grasp part 34d extends further from an outer perimetric edge of the conical-projections sheet 23 in the horizontal direction radially outward. Specifically, the grasp part 34d has the shape of a ring that is provided on the outer perimeter of the main-body part 34c. The grasp part 34d is a member used for peeling the conical-projections forming sheet 34 from the conical-projections sheet 23. Accordingly, when using the support-body-attached, conical-projections sheet 3, the operation of peeling the conical-projections forming sheet 34 from the conical-projections sheet 23 becomes easy by grasping the grasp part 34d.

Furthermore, the reason it becomes possible to form the grasp part 34d on the conical-projections forming sheet 34 is that, as shown in FIG. 22(b), when the plurality of conical-projections sheets 23 are punched out from the solidified conical-projections materials 56, the blank 107, which becomes the conical-projections forming sheets 34, is not punched out. Consequently, this ensures the state in which the conical-projections forming sheets 34 are larger than the conical-projections sheets 23.

As shown in FIG. 23, the support-body-attached, conical-projections sheet 3 is movably disposed inside the packaging member 7 and the sealing sheet 9. Furthermore, in the present embodiment, the packaging member 7 does not have the stepped surface 35.

Figure 25:
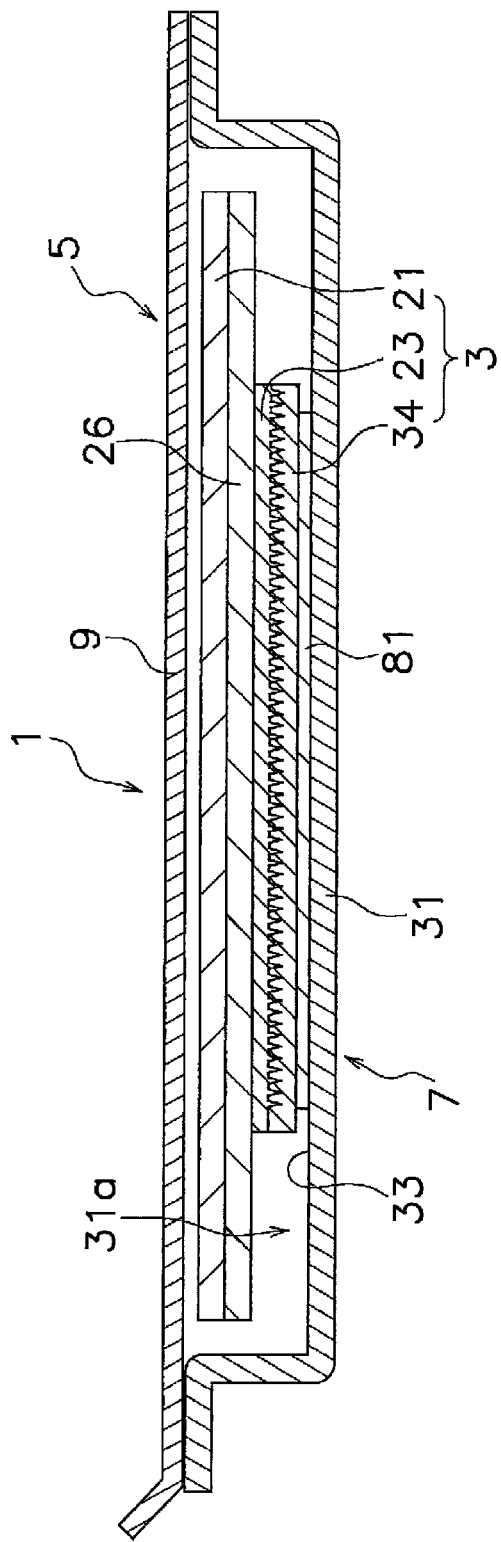
FIG. 25 is a schematic cross-sectional view of the conical-projections-sheet packaging body (fifth embodiment)

In addition, the support-body-attached, conical-projections sheet 3 may be fixed to the packaging member 7 by, for example, a means such as that used in the first embodiment (FIG. 4) or a fifth embodiment (FIG. 25).

(5) Fourth Embodiment

In the first embodiment, the support-body-attached, conical-projections sheet 3 is fixed to the packaging member 7, but it does not necessarily have to be fixed.

Figure 24:
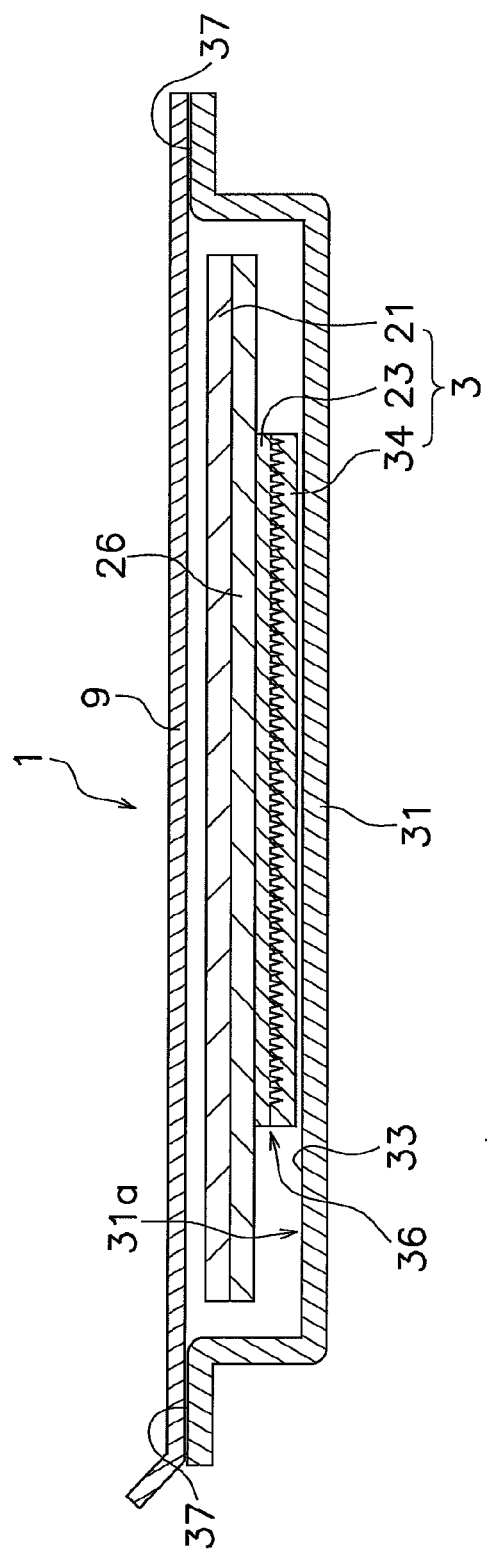
FIG. 24 is a schematic cross-sectional view of the conical-projections-sheet packaging body (fourth embodiment)

FIG. 24 is a schematic cross-sectional view of the conical-projections-sheet packaging body. In the present embodiment, the support-body-attached, conical-projections sheet 3, which is the same as that in the first embodiment, is movably disposed inside the packaging member 7 and the sealing sheet 9. Furthermore, in the present embodiment, the packaging member 7 does not have the stepped surface 35.

(6) Fifth Embodiment

In the third embodiment and the fourth embodiment, the support-body-attached, conical-projections sheet 3 is not fixed to the packaging member 7, but the support-body-attached, conical-projections sheet 3 may be fixed to the packaging member 7 by a method that differs from that in the first embodiment.

The state in which the support-body-attached, conical-projections sheet 3 is housed in the packaging member 7 and the sealing sheet 9 will be explained, with reference to FIG. 25. FIG. 25 is a schematic cross-sectional view of the conical-projections-sheet packaging body.

In the figure, the support-body-attached, conical-projections sheet 3, which is the same as that in the first embodiment, is immovably disposed inside the packaging member 7 and the sealing sheet 9. Specifically, a bonding layer 81 is provided on the bottom surface 33 of the housing part 31 of the packaging member 7. The support-body-attached, conical-projections sheet 3 is fixed to the packaging member 7 via the bonding layer 81. More specifically, the conical-projections forming sheet 34 is fixed to the bottom surface 33 of the packaging member 7 via the bonding layer 81.

In the state in which the conical-projections-sheet packaging body 1 has been thusly completed, the conical-projections sheet 23 maintains the state in which it is fixed to the packaging member 7 via the bonding layer 81. In other words, by virtue of the conical-projections forming sheet 34 being fixed to the package member 5, the support body 21, the conical-projections sheet 23, and the conical-projections forming sheet 34 are positioned inside the package member 5. In so doing, the conical projections 23b are protected when the conical-projections-sheet packaging body 1 is transported or used. In particular, because the positioning of the conical-projections sheet 23, etc. inside the package member 5 is accomplished by fixing the conical-projections forming sheet 34 to the package member 5, the plurality of conical projections 23b of the conical-projections sheet 23 can be protected with a simple structure and method.

Figure 26:
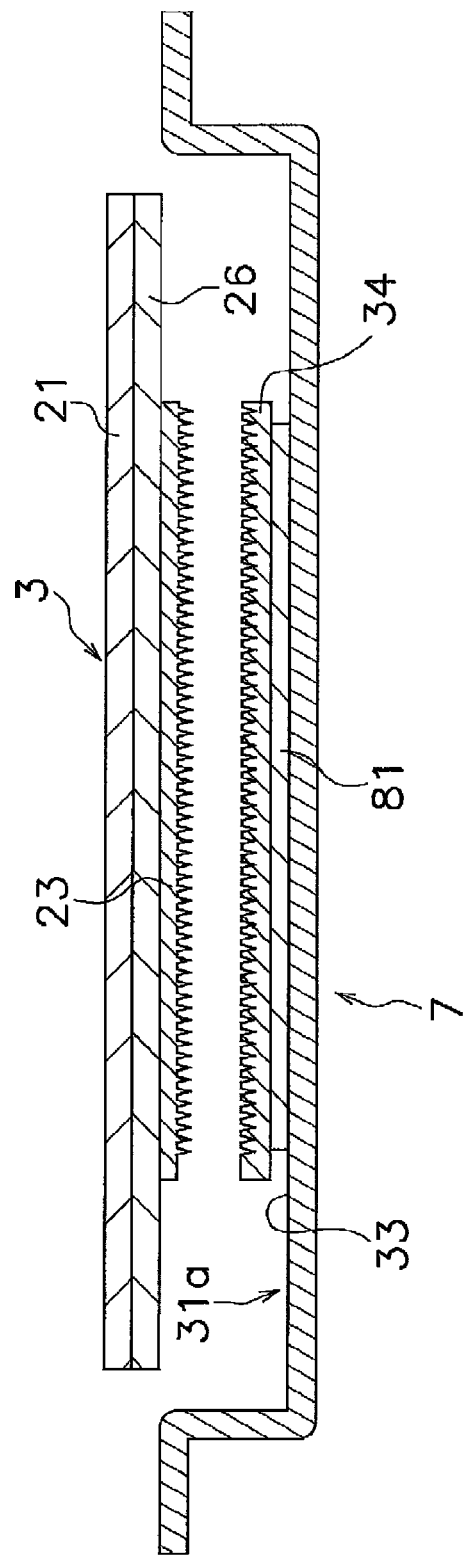
FIG. 26 is a schematic cross-sectional view for explaining, according to the fifth embodiment, the state in which the support-body-attached, conical-projections sheet has been peeled from the conical-projections forming sheet.

The operation of peeling the support-body-attached, conical-projections sheet 3 from the conical-projections forming sheet 34 will now be explained, with reference to FIG. 26. FIG. 26 is a schematic cross-sectional view for explaining, according to the fifth embodiment, the state in which the support-body-attached, conical-projections sheet has been peeled from the conical-projections forming sheet. As shown in the figure, the user holds the support body 21 and peels the support-body-attached, conical-projections sheet 3 from the packaging member 7. In so doing, the conical-projections forming sheet 34 remains on the packaging member 7 side; that is, the conical-projections sheet 23 is peeled from the conical-projections forming sheet 34. As described above, by peeling the support-body-attached, conical-projections sheet 3 from the packaging member 7, the conical-projections forming sheet 34 can be separated from the conical-projections sheet 23 at the same time. As a result, when the user peels the support-body-attached, conical-projections sheet 3 from the packaging member 7, the conical-projections sheet 23 in the state in which the plurality of conical projections 23b are exposed is obtained; as a result, the support-body-attached, conical-projections sheet 3 can be used immediately.

(7) Points in Common Among the Embodiments

The first through fifth embodiments have the below-mentioned points in common.

A method of manufacturing a packaging body (e.g., the conical-projections-sheet packaging body 1) according to one aspect of the present invention includes the following steps:

a step (e.g., refer to FIG. 10 to FIG. 13) that forms a plurality of conical-recess parts (e.g., the conical-recess parts 34b) on the conical-projections forming sheet (e.g., the conical-projections forming sheet 34);

a step (e.g., refer to FIG. 14 to FIG. 18) that, by supplying the conical-projections material 56 to the conical-projections forming sheet, forms the conical-projections sheet (e.g., the conical-projections sheet 23) including the base sheet (e.g., the base sheet 23a) and the plurality of conical projections (e.g., the conical projections 23b), which are formed on the surface of the base sheet and disposed inside the plurality of conical-recess parts;

a step (e.g., refer to FIG. 21, FIG. 22, and FIG. 23) that punches out the conical-projections forming sheet and the conical-projections sheet to form a plurality of sets of the conical-projections forming sheets and the conical-projections sheets; and a step (e.g., refer to FIG. 4, FIG. 23, FIG. 24, and FIG. 25) that uses the package member (e.g., the package member 5) to package a set of the conical-projections sheet and the conical-projections forming sheet, which are tightly adhered to one another.

In this manufacturing method, the conical-projections sheet is formed in the conical-projections forming sheet, and that state when formed is maintained. Specifically, the plurality of conical projections of the conical-projections sheet are formed by the plurality of conical-recess parts of the conical-projections forming sheet and is also subsequently protected by the plurality of conical-recess parts. That is, the plurality of conical projections of the conical-projections sheet are reliably protected.

In addition, this manufacturing method further includes a step of punching out the conical-projections forming sheets and the conical-projections sheets to form a plurality of sets of the conical-projections forming sheets and the conical-projections sheets. Accordingly, the plurality of conical-projections-sheet packaging bodies can be manufactured in a short time.

(8) Other Embodiments

The above explained one embodiment of the present invention, but the present invention is not limited to the abovementioned embodiment, and it is understood that various modifications may be effected without departing from the gist of the invention. In particular, the embodiments and modified examples written in the present specification can be arbitrarily combined as needed.

(a) In the abovementioned embodiments, the support body 21 is composed of one sheet, but the support body may be composed of a plurality of sheets.

(b) In the abovementioned embodiments, each support body 21 includes the adhesive layer, which covers the entire surface of the conical-projections sheet 23 and further extends entirely around the outer-perimeter side; however, the shape of the support body, the positional relationship with the conical-projections sheet, the shape of the adhesive layer, and the like can be modified as appropriate. In particular, the shape of the protruding part (the portion that is adhered onto the stepped surface 35) of the support body 21 is the ring shape in the abovementioned embodiments, but the shape is not limited thereto.

(c) In the abovementioned embodiments, the cutting of the various sheets is performed by a trimming die but may be performed by some other means such as a laser.

(d) In the abovementioned embodiments, the grasp part 34d of the conical-projections forming sheet 34 is formed into a ring shape over the entire outer perimeter of the main-body part 34c, but the shape is not particularly limited. For example, the grasp part may be formed over only part of the outer perimeter of the main-body part.

(e) In the abovementioned embodiments, the number of the housing parts 31 of the conical-projections-sheet packaging body 1 is one, but there may be a plurality of housing parts.

(f) In the abovementioned embodiments, the sealing sheet is simply adhered onto the packaging member, but the sealing sheet may be fixed to the packaging member using vacuum packaging (an evacuating process). In this case, by using vacuum packaging, the gap between the packaging member and the sealing sheet is eliminated; as a result, the conical-projections sheet becomes immovable between the packaging member and the sealing sheet. Consequently, the plurality of conical projections of the conical-projections sheet tend not to break.

The present invention can be broadly applied to methods of manufacturing a conical-projections-sheet packaging body including a plurality of conical projections.

The invention claimed is:

1. A method of manufacturing a conical-projections-sheet packaging body comprising:
    forming a plurality of conical-recess parts on a conical-projections forming sheet;
    forming, by supplying a conical-projections material to the conical-projections forming sheet, a conical-projections sheet including a base sheet and a plurality of conical projections formed on a first surface of the base sheet and disposed inside the plurality of conical-recess parts;
    fixing a support member onto a second surface of the base sheet of the conical-projections sheet;
    forming a plurality of sets of the conical-projections forming sheets and the conical-projections sheets on the support member by punching out the conical-projections forming sheet and the conical-projections sheet such that the support member is not cut and removing waste parts;
    punching out the support member corresponding to shapes of the sets such that a projecting portion is formed that projects from the set in a horizontal direction, on the support member; and
    using a package member to package the support member, the conical-projections sheet, and the conical-projections forming sheet.

2. The method of manufacturing the conical-projections-sheet packaging body according to claim 1, wherein
    the using a package member to package the support member includes positioning the support body, the conical-projections sheet, and the conical-projections forming sheet inside the package member by adhering the protruding portion to a part of the package member.

3. The method of manufacturing the conical-projections-sheet packaging body according to claim 1, wherein
    the using a package member to package the support member includes fixing the conical-projections forming sheet to the package member.

4. A conical-projections-sheet packaging body manufactured by a method of manufacturing the conical-projections-sheet packaging body, the method comprising:
    forming a plurality of conical-recess parts on a conical-projections forming sheet;
    forming, by supplying a conical-projections material to the conical-projections forming sheet, a conical-projections sheet including a base sheet and a plurality of conical projections formed on a first surface of the base sheet and disposed inside the plurality of conical-recess parts;
    fixing a support member onto a second surface of the base sheet;
    forming a plurality of sets of the conical-projections forming sheets and the conical-projections sheets on the support member by punching out the conical-projections forming sheet and the conical-projections sheet such that the support member is not cut and removing waste parts;
    punching out the support member corresponding to shapes of the sets such that a projecting portion is formed that projects from the set in a horizontal direction, on the support member; and
    using a package member to package the support member, the conical-projections sheet, and the conical-projections forming sheet, the package member including a recessed-housing part having a bottom surface and an upper surface upwardly open to house the support member, the conical-projections sheet and the conical-projections forming sheet, and a sealing sheet fixed to the recessed-housing part so as to cover the opening, and
    the conical-projections forming sheet being fixed to the bottom surface.

* * * * *